(12) United States Patent
Yamaguchi

(10) Patent No.: US 8,148,431 B2
(45) Date of Patent: Apr. 3, 2012

(54) OSTEOGENESIS PROMOTER CONTAINING β-CRYPTOXANTHIN AS THE ACTIVE INGREDIENT

(75) Inventor: Masayoshi Yamaguchi, Shizuoka (JP)

(73) Assignee: Kemin Health, L.C., Des Moines, IA (US)

( * ) Notice: Subject to any disclaimer, the term of this patent is extended or adjusted under 35 U.S.C. 154(b) by 1001 days.

(21) Appl. No.: 10/532,775

(22) PCT Filed: Oct. 3, 2003

(86) PCT No.: PCT/JP03/13561
§ 371 (c)(1),
(2), (4) Date: Oct. 7, 2005

(87) PCT Pub. No.: WO2004/037236
PCT Pub. Date: May 6, 2004

(65) Prior Publication Data
US 2006/0106115 A1 May 18, 2006

(30) Foreign Application Priority Data
Oct. 25, 2002 (JP) .................... 2002-311930

(51) Int. Cl.
*A61K 31/07* (2006.01)
(52) U.S. Cl. ........................................... 514/725
(58) Field of Classification Search .............. 514/725
See application file for complete search history.

(56) References Cited

U.S. PATENT DOCUMENTS

| 5,424,331 A | * | 6/1995 | Shlyankevich | ............... 514/456 |
| 5,935,996 A | | 8/1999 | Yamaguchi | |

FOREIGN PATENT DOCUMENTS

| CA | 2382008 | 3/2001 |
| JP | 7-215849 | 8/1995 |
| JP | 10-36256 | 2/1998 |
| JP | 10-114653 | 5/1998 |
| JP | 10-218767 | 8/1998 |
| JP | 10-279492 | 10/1998 |
| JP | 11-46770 | 2/1999 |
| JP | 11-155577 | 6/1999 |
| JP | 2000-23637 | 1/2000 |
| JP | 2000-136181 | 5/2000 |
| JP | 2000-191526 | 7/2000 |
| JP | 2001-302539 | 10/2001 |
| JP | 2001-521943 | 11/2001 |
| WO | WO 99/23587 A2 | 5/1999 |
| WO | WO 00/06141 | 2/2000 |

OTHER PUBLICATIONS

Medline Abstract, (accession No. 8293487), Johansen et al., Drugs & Aging, (Feb. 1996), vol. 8, No. 22, pp. 113-126.*
Medline Abstract (accession No. 1998228764), Frost, Medicina, (1997), vol. 57, Suppl 1, pp. 119-126.*
Medline Abstract (accession No. 941233361), Balliere's Clinical Rheumatology, (Oct. 1993), vol. 7, No. 3, pp. 515-534, Boyle et al.*
The Merck Index, 11th Edition, published 1989 by Merck & Co., Inc., (NJ), p. 409, citation # 2612 "Cryptoxanthin".*
Lin, S.D. and A.O. Chen, "Major Carotinoids in Juices of Ponkan Mandarin and Liucheng Orange," *Journal of Food Biochemistry*, vol. 18, 1995, pp. 273-283, USA.
Walter, Klaus and Christian Schutt, *Methods of Enzymatic Analysis*, vol. 2, 1965, pp. 856-864, USA.

* cited by examiner

*Primary Examiner* — Raymond Henley, III
(74) *Attorney, Agent, or Firm* — Kent A. Herink; Emily E. Harris

(57) ABSTRACT

It is intended to provide an osteogenesis promoter having a remarkable effect of positively promoting osteogenesis and thus preventing/treating bone diseases; a preventive/a remedy for bone diseases such as osteoporosis having both of an osteogenesis-promoting effect and a bone resorption-inhibiting effect; and a method of screening an active ingredient for preventing/treating bone diseases by using a compound having both of an osteogenesis-promoting effect and a bone resorption-inhibiting effect as a lead compound. It is confirmed that beta-cryptoxanthin, which occurs in a large amount in peel and sarcocarp of satsuma orange, has an osteogenesis-promoting effect and a therapeutic effect on bone disease. Thus, beta-cryptoxanthin or its composition is used as an osteogenesis promoter, a preventive/a remedy for bone diseases, a functional food or a food material for preventing/treating bone diseases and a feed composition.

9 Claims, 12 Drawing Sheets

Bone calcium level (mg/g dry weight)

Bone alkaline phosphatase activity (nmol/min/mg protein)

Bone DNA level (mg/g bone wet weight)

Bone calcium level (mg/g dry weight)

Bone alkaline phosphatase activity (nmol/min/mg protein)

Bone DNA level (mg/g bone wet weight)

Bone calcium level (mg/g dry weight)

Bone alkaline phosphatase activity (nmol/min/mg protein)

Bone DNA level (mg/g bone wet weight)

Bone calcium level (mg/g dry weight)

Bone alkaline phosphatase activity (nmol/min/mg protein)

Bone DNA level (mg/g bone wet weight)

Bone calcium level (mg/g dry weight)

Bone calcium level (mg/g dry weight)

Bone calcium level (mg/g dry weight)

Bone calcium level (mg/g dry weight)

Bone calcium level (mg/g dry weight)

Bone calcium level (mg/g dry weight)

Bone DNA level (mg/g bone wet weight)

Bone calcium level (mg/g dry weight)

Bone alkaline phosphatase activity (μmol/min/mg protein)

Bone DNA level (mg/g bone wet weight)

OSTEOGENESIS PROMOTER CONTAINING β-CRYPTOXANTHIN AS THE ACTIVE INGREDIENT

TECHNICAL FIELD

The present invention relates to an osteogenesis promoter and a preventive/remedy for bone diseases such as osteoporosis, containing β-cryptoxanthin as the active ingredient; a β-cryptoxanthin-containing functional food or food material and feed composition for the prevention/treatment of bone diseases such as osteoporosis; and a method of screening an active ingredient for promoting osteogenesis or for preventing/treating bone diseases by using β-cryptoxanthin as lead compound.

TECHNICAL BACKGROUND

It is considered that various bone diseases occur because, for example, calcium content of bones is decreased by the bone metabolism and insufficient osteogenesis. Typical bone diseases are, for example, fracture, osteomalacia, osteopenia, osteoporosis, back pain and low back pain. In those bone diseases, osteoporosis has a pathology caused by the following reasons: The bone mass is decreased as the balance of the bone resorption and the bone formation is lost by aging and, accordingly, the hone resorption is relatively increased to reduce the bone mass. As a result, the bone strength is decreased by the change in the fine structure of the bones to easily cause the fracture. Particularly in females, the bone mass is rapidly decreased after menopause, oophorectomy, etc. Osteoporosis not only causes the fractures or sharp pain but it also maces the patients bedridden, particularly in cases of elderly people. Under these circumstances, an effective cure is demanded for improving the quality of life in an aging society. Because it is difficult to cure patients with osteoporosis after the onset, the following points are now fully recognized: It is important to prevent this disease and it is also indispensable to start increasing of the amount of the bones in juvenile period. In addition, it is essential that nutrients required for the formation of bones and foods accelerating the formation of them must be taken everyday. As foods for strengthening the bones, calcium, magnesium and vitamin D are mainly taken nowadays. Casein phosphopeptide or the like for accelerating the absorption of calcium through the intestinal tracts is also used.

As the remedies for bone diseases such as osteoporosis, active vitamin $D_3$, a female sex hormone (estrogen), calcitonin and ipriflavones are clinically used. Recently, a medicine for osteoporosis having an effect of polyisoprenoid derivatives typified by vitamin $K_2$ for inhibiting the formation of osteoclasts was developed (Japanese Patent Kokai No. Hei 7-215849). There have been known a bone reinforcing agent containing casein phosphopeptide and genistein as the active ingredients (Japanese Patent Kokai No. 2001-302539); a composition for accelerating the bone formation, which is effective against osteoporosis and which contains saponin, daidzin, daidzein, genistin and genistein as the main active ingredients (Japanese Patent Kokai No 2000-191526); a composition for increasing the bone mass, which is effective against osteoporosis and which contains a Japanese horseradish extract as the active ingredient (Japanese Patent Kokai No Hei 10-279492); a remedy for bone diseases containing zinc acexamate as the active ingredient (Japanese Patent Kokai No. 10-218767); a composition for accelerating the bone formation and preventing the reduction in bone mineral density, which contains isoflavon as the main active ingredient (Japanese Patent Kokai No. Hei 10-114653); and an anti-osteoporotic composition containing reinforced vitamin K, and zinc (Japanese Patent Kokai No. Hei 10-36256).

On the other hand, β-cryptoxanthin (molecular weight: 552) is known as a carotenoid soluble in ethanol. β-Cryptoxanthin is contained in citrus fruits, particularly in Satsuma oranges in an amount of 1 to 2 mg in each orange. β-cryptoxanthin has characteristic properties of provitamin A. In addition, in the recent investigation of anticancer substances, it was found that β-cryptoxanthin has an anticancer effect stronger than that of β-carotene which is a carotenoid contained in green and yellow vegetables such as carrots and therefore, β-cryptoxanthin is becoming the center of attention (Biol. Pharm. Bull 18, 2, 227, 1995). Because β-cryptoxanthin is thus an important anti-carcinogenic component, techniques are now being developed for producing citrus fruits of a high quality having a β-cryptoxanthin content equal to that of the Satsuma oranges, for isolating genes for synthesizing β-cryptoxanthin (Japanese Patent Kokai Nos. Hei 11-155577 and Hei 11-46770), and for isolating a large amount of β-cryptoxanthin from the citrus fruits for the purpose of developing citrus fruits having an increased β-cryptoxanthin content and processed citrus fruit foods.

Methods for separating β-cryptoxanthin from citrus fruits such as Satsuma oranges are well known (Report of the Agricultural Department of Okayama University 69, 17-25, 1987, Tokyo Medical College Bulletin 18, 1-7, 1992 and (Journal of Food Biochemistry 18, 273-283, 1995) Recently, the following methods were proposed: a method for producing β-cryptoxanthin of a high purity which comprises the steps of pressing orange juice, obtaining an extract containing β-cryptoxanthin from the resultant precipitate width a solvent, hydrolyzing the extract, introducing the hydrolyzate into the first column filled with silica powder having an average particle diameter of 10 to 80 μm together with a primary development solvent at a linear velocity of at least 2 cm/min to separate a fraction containing. β-cryptoxanthin, removing the solvent, and introducing the isolated product into the second column filled with octadecylsilane silica having an average particle diameter of 10 to 80 μm together with a secondary development solvent at a linear velocity of at least 2 cm/min to separate the fraction containing at least 95% by weight of β-cryptoxanthin (Japanese Patent Kokai No. 2000-136181); a process for producing pulps having a high carotenoid content, which comprises the steps of squeezing citrus fruits, filtering or sieving the obtained juice, centrifuging the obtained the juice, adding an enzyme to the obtained precipitate, freezing the resultant mixture, thawing the mixture and dehydrating the obtained product; and a method for producing pulp containing an increased amount of carotenoid, β-cryptoxanthin, etc. and powder thereof which comprises the steps of repeating a process of adding water to a pulp having a high carotenoid content and dehydrating the pulp, and then drying and pulverizing the pulp (Japanese Patent Kokai No. 2000-23637).

For rapidly retrieving analogs which might have the activity of the lead compound, there is known a method for producing chemically possible combinatorial products from a large data base of finger prints having 3D multiple stereo-structure and screening the products, which comprises the steps of temporarily binding the radical with a bulky space keeping group, registering the 3D model of the radical in a combinatorial ghost data base, detecting an optional atom having characteristic physical properties of pharmacophore type for an accessible optional molecular structure in the ghost data base; calculating all the distances between atoms relating to the whole stereostructure of the molecule, for the pair of the pharmacophore detected in each molecular structure to prepare the distance distribution density; preparing a stereostructure finger print vector including all the distance distribution density of the pair of the pharmacophore; defining the gauge function for each finger print for explaining the relative importance of the characteristics of the pharmacophore; preparing the finger print of the lead compound, comparing the finger print with each finger print of a possible library in the gauge function for making the lead compound maximum, and retrieving the possible library molecule for obtaining a mark below a specified threshold by the gauge function (Japanese Patent Publication No. 2001-521943).

It was reported that eight therapeutic agents now approved in Japan for bone diseases typified by osteoporosis are bone resorption-inhibitors (inhibiting the solution of bones) and also that only statin, which is a mevalonic acid synthetic inhibitors has the osteogenesis promoting effect. However, this finding is only on the gene level and, in fact, the osteogenesis promoting effect of statin was only weak. The object of the present invention is to provide an osteogenesis promoter having a remarkable effect of positively promoting osteogenesis and thus preventing/treating bone diseases, a preventive/a remedy for bone diseases such as osteoporosis having both of an osteogenesis-promoting effect and a bone resorption-inhibiting effect, and a method of screening an active ingredient for preventing/treating bone diseases by using a compound having both of an osteogenesis-promoting effect and a bone resorption-inhibiting effect as a lead compound.

The inventors have found that β-cryptoxanthin, which is contained in a large amount in peel and sarcocarp of Satsuma orange, has an osteogenesis-promoting effect and effect of preventing/treating bone diseases. Namely, the inventors made experiments wherein diaphysis and metaphysis tissue of a femur were cultured in a culture medium containing β-cryptoxanthin, then calcium level in the bone tissue, the amount of the expressed bone calcification accelerating enzyme and bone DNA level which is the index of the number of the cells in the bone tissue were determined to confirm a significant increase in all the cases. In the experiments, the inventors have found that β-cryptoxanthin accelerates the synthesis of protein in the cancellous bone in the femur tissue (tissue of the metaphysis) and cortical bone (tissue of the diaphysis) to promote the osteogenesis. The inventors cultured a bone tissue in the presence of both parathyroid hormone (PTH), having an effect of dissolving the bone mineral (bone resorption) and a physiological role of causing pathology of osteoporosis due to aging, and β-cryptoxanthin to confirm that the reduction in amount of calcium in the tissue of the diaphysis and tissue of the metaphysis can be significantly controlled. When the inventors orally administered β-cryptoxanthin to rats, all of calcium level in the diaphysis and metaphysis tissue the amount of the expressed bone calcification accelerating enzyme and bone DNA level which is the index of the number of cells in the bone tissue were significantly increased. The inventors have thus confirmed that the oral administration of β-cryptoxanthin effectively increases the bone mass. From those facts, it was made evident that β-cryptoxanthin accelerates the osteogenesis and also inhibits the bone resorption to exhibit the effect of keeping and/or increasing the bone mineral density and also to function as an anti-osteoporotic factor. It was confirmed by experiences that the effects confirmed in such a tissue culture system are almost 100% effective also in peroral experiments. The present invention has been completed on the basis of these findings.

DISCLOSURE OF THE INVENTION

Namely, the present invention relates to an osteogenesis promoter containing β-cryptoxanthin as an active ingredient, an osteogenesis promoter containing a β-cryptoxanthin-containing composition as an active ingredient, the osteogenesis promoter, wherein the β-cryptoxanthin-containing composition is obtained by treating Satsuma orange, a preventive/remedy for bone diseases, containing β-cryptoxanthin as an active ingredient, a preventive/remedy for bone diseases, containing a β-cryptoxanthin-containing composition as an active ingredient, the preventive/remedy for bone diseases, wherein the β-cryptoxanthin-containing composition is obtained by treating Satsuma orange, the preventive/remedy for bone diseases, wherein the bone disease is osteoporosis, functional foods or food materials for preventing or treating bone diseases, which contain β-cryptoxanthin, functional foods or food materials for preventing or treating bone diseases, which contains a β-cryptoxanthin-containing composition, the functional foods or food materials for preventing or treating bone diseases, wherein the β-cryptoxanthin-containing composition is obtained by treating Satsuma orangeand the functional foods or food materials for preventing or treating bone diseases, wherein the bone disease is osteoporosis.

The present invention further relates to a feed composition containing β-cryptoxanthin, a feed composition containing a β-cryptoxanthin-containing composition, the feed, wherein the β-cryptoxanthin-containing composition is obtained by treating Satsuma orange , a method of screening an active ingredient for promoting osteogenesis or preventing/treating bone diseases, wherein β-cryptoxanthin is used as the lead compound, the method of screening an active ingredient for promoting osteogenesis or preventing/treating bone diseases, wherein the bone disease is osteoporosis, an osteogenesis promoter or a preventive/remedy for bone diseases, containing β-cryptoxanthin obtained by the screening method as the lead compound, and the osteogenesis promoter or a preventive/remedy for bone diseases, containing β-cryptoxanthin as the lead compound wherein the bone disease is osteoporosis.

BEST MODE FOR CARRYING OUT THE PRESENT INVENTION

Figure 1:
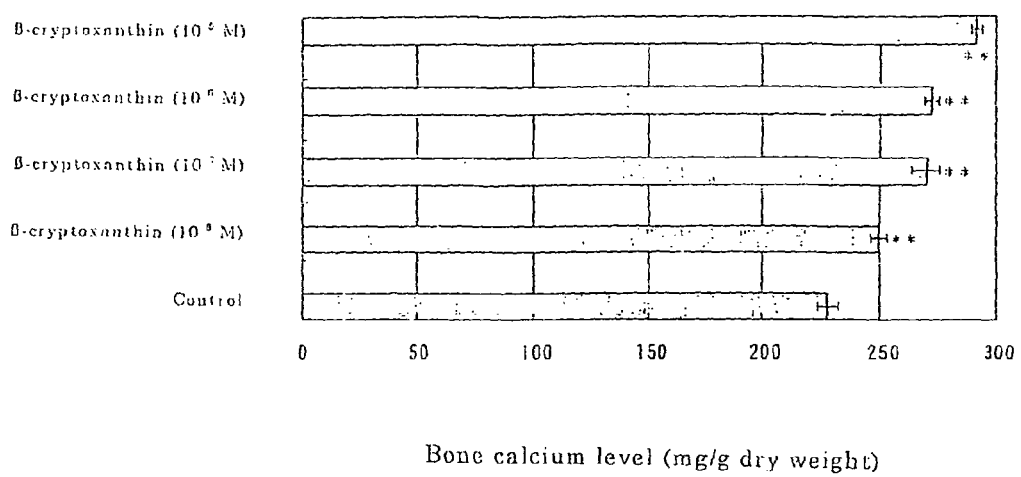
FIG. 1 shows the effects of β-cryptoxanthin of the present invention on the results of the determination of bone calcium level in the diaphysis tissue.
Figure 2:
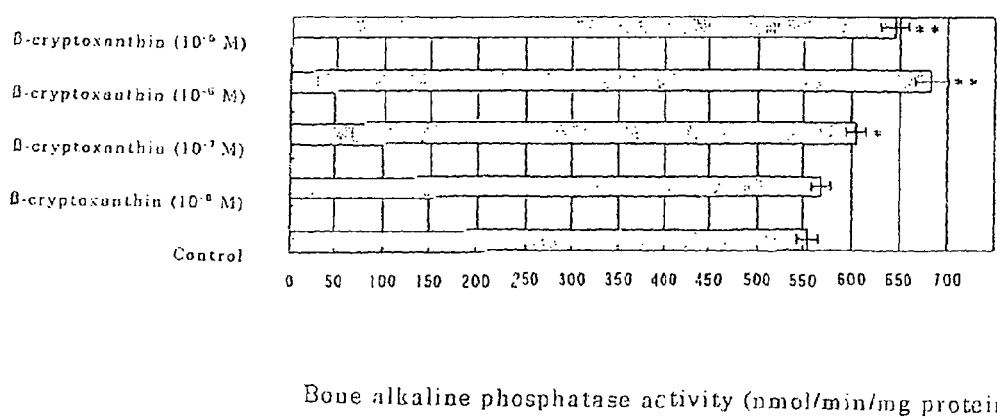
FIG. 2 shows the effects of β-cryptoxanthin of the present invention on the results of the determination of bone alkaline phosphatase activity in the diaphysis tissue.
Figure 3:
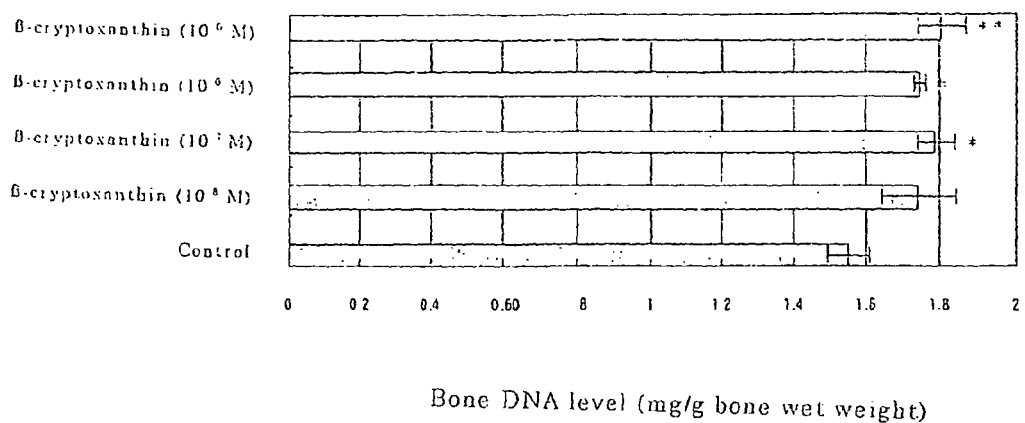
FIG. 3 shows the effects of β-cryptoxanthin of the present invention on the results of the determination of bone DNA level in diaphysis tissue.
Figure 4:
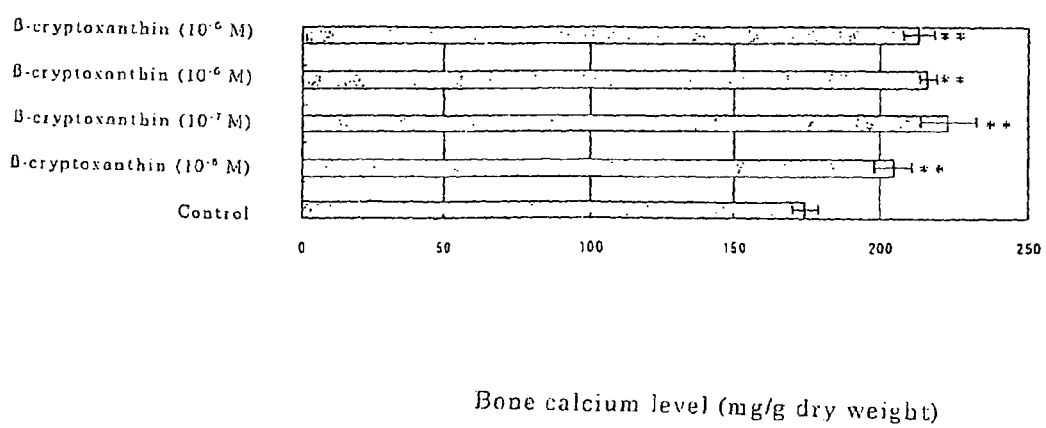
FIG. 4 shows the effects of β-cryptoxanthin of the present invention on the results of the determination of bone calcium level in the metaphysis tissue.
Figure 5:
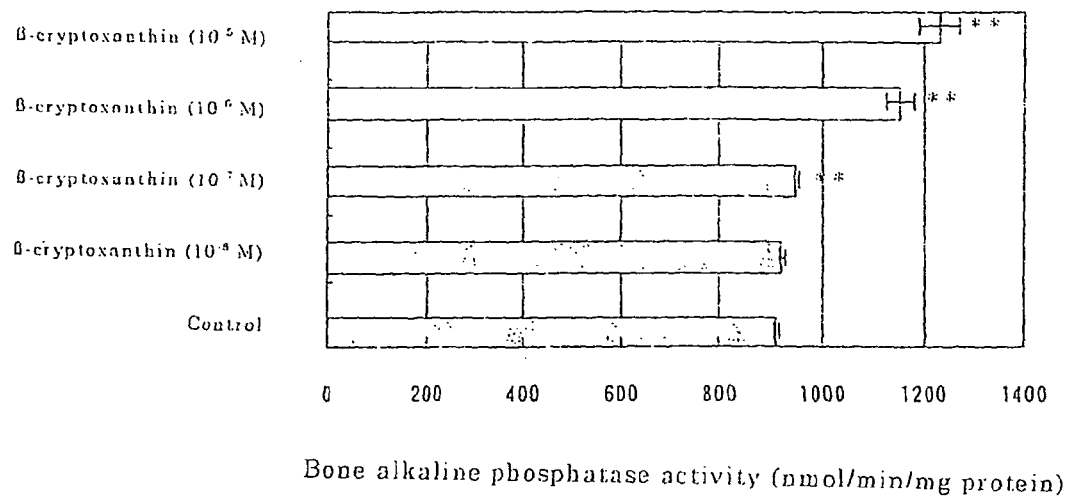
FIG. 5 shows the effects of β-cryptoxanthin of the present invention on the results of the determination of bone alkaline phosphatase activity in the metaphysis tissue.
Figure 6:
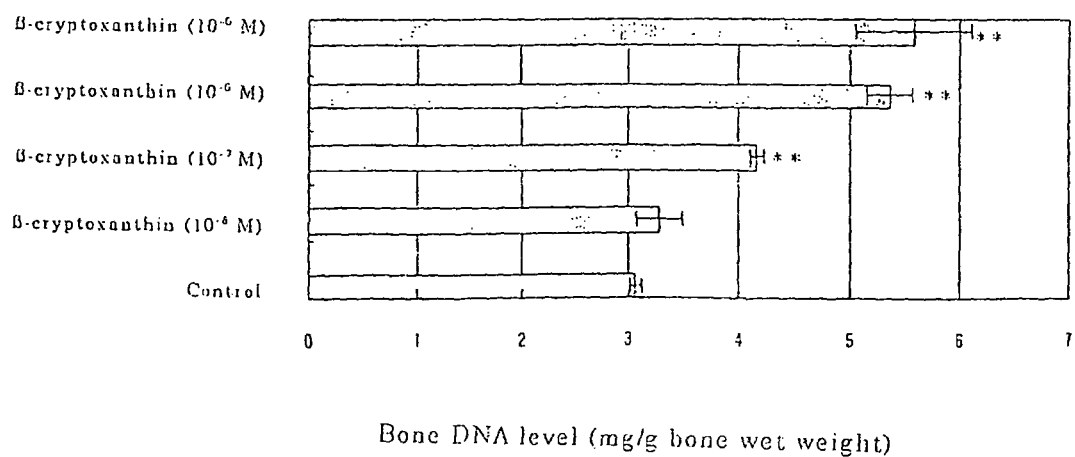
FIG. 6 shows the effects of β-cryptoxanthin of the present invention on the results of the determination of bone DNA level in the metaphysis tissue.
Figure 7:
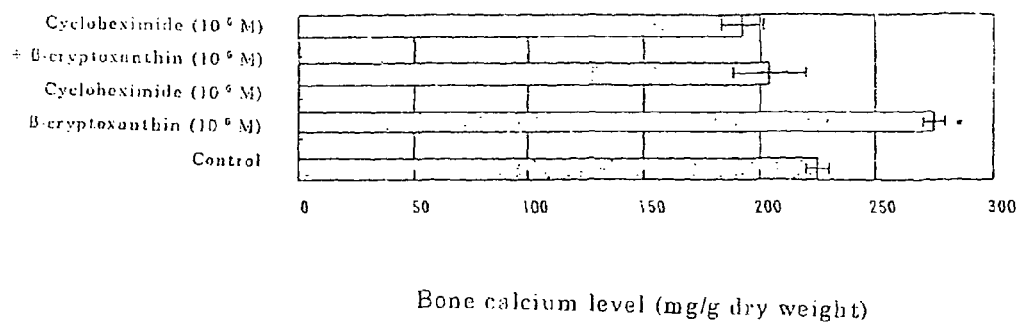
FIG. 7 shows the results of the determination of bone calcium level in the diaphysis tissue in the coexistence of β-cryptoxanthin of the present invention and a protein synthesis inhibitor.
Figure 8:
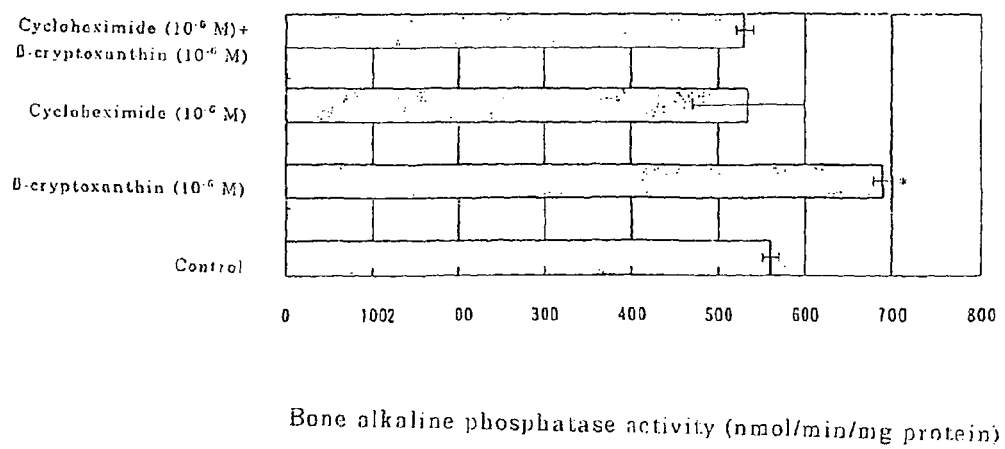
FIG. 8 shows the results of the determination of bone alkaline phosphatase activity in the diaphysis tissue in the coexistence of β-cryptoxanthin of the present invention and a protein synthesis inhibitor
Figure 9:
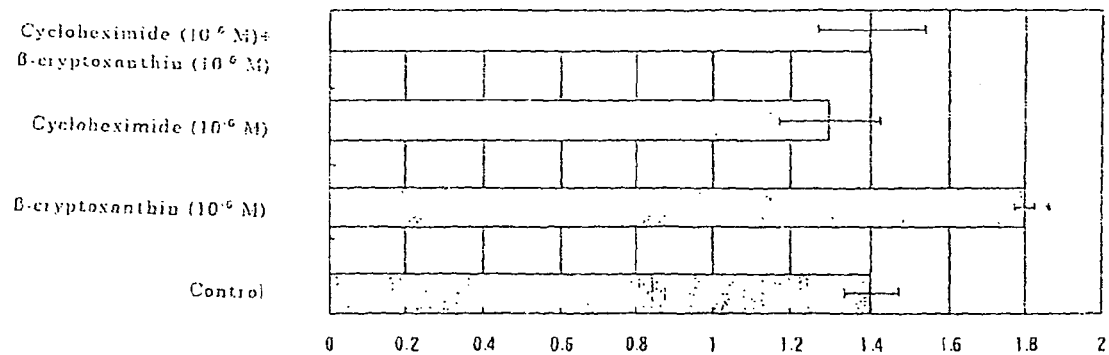
FIG. 9 shows the results of the determination of bone DNA level in the diaphysis tissue in the coexistence of β-cryptoxanthin of the present invention and a protein synthesis inhibitor.
Figure 10:
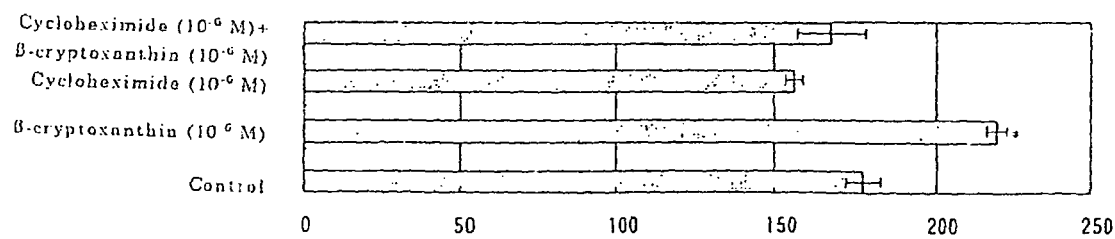
FIG. 10 shows the results of the determination of bone calcium level in the metaphysis tissue in the coexistence of β-cryptoxanthin of the present invention and a protein synthesis inhibitor.
Figure 11:
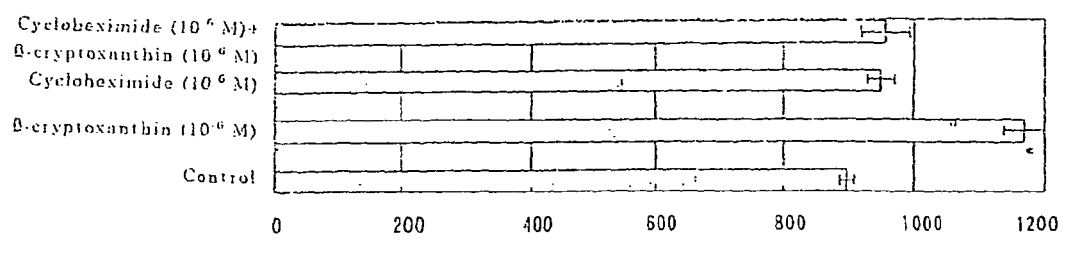
FIG. 11 shows the results of the determination of bone alkaline phosphatase activity in the metaphysis tissue in the coexistence of β-cryptoxanthin of the present invention and a protein synthesis inhibitor.
Figure 12:
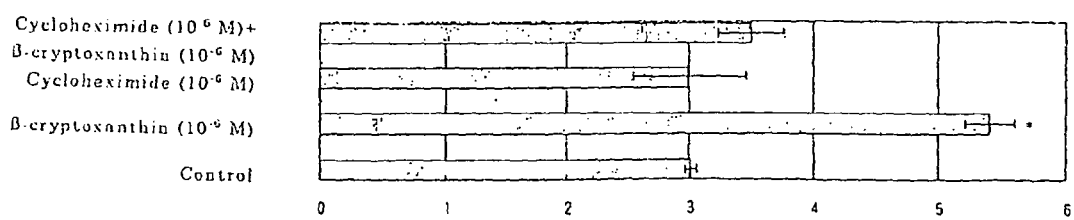
FIG. 12 shows the results of the determination of bone DNA level in the metaphysis tissue in the coexistence of β-cryptoxanthin of the present invention and a protein synthesis inhibitor.

The osteogenesis promoter of the present invention is not particularly limited so far as it contains β-cryptoxanthin or a β-cryptoxanthin-containing composition as the active ingredient. The preventive/remedy for bone diseases of the present invention is also not particularly limited so far as it contains β-cryptoxanthin or a β-cryptoxanthin-containing composition as the active ingredient. The functional foods or food materials for preventing or treating bone diseases of the present invention are not particularly limited so far as they are foods or food materials containing β-cryptoxanthin or a β-cryptoxanthin-containing composition and having the function of preventing or treating bone diseases and usable for preventing or treating the bone diseases. The feed composition of the present invention is also not particularly limited so far as it contains β-cryptoxanthin or a β-cryptoxanthin-containing composition. The bone diseases are, for example, bone fractures, osteomalacia, osteopenia, osteoporosis and back pain and low back pain. In particular, examples of the bone diseases for which the osteogenesis promoter is particularly recommended are osteoporosis such as postmenopausal osteoporosis, estrogen-deficiency osteoporosis, senile osteoporosis and steroid-induced osteoporosis, as well as metabolic bone diseases such as osteomalacia.

A method of obtaining β-cryptoxanthin or a β-cryptoxanthin-containing composition is not particularly limited and a known method such as a method wherein it is extracted/produced from citrus fruits or a method wherein a gene encoding a β-cryptoxanthin-producing enzyme is utilized is employed. Preferred starting materials for β-cryptoxanthin and the β-cryptoxanthin-containing composition are Satsuma oranges containing β-cryptoxanthin in an amount of 1 to 2 mg/orange which is at least 60 times as much as β-cryptoxanthin content of other citrus oranges such as other oranges, grape fruits and lemons. In Satsuma oranges, particularly preferred oranges are those of varieties having a high 3-cryptoxanthin content such as Sugiyama oranges containing about 8 mg of β-cryptoxanthin per 100 g of the peel (flavedo) and about 1 mg of β-cryptoxanthin per 100 mg of the juice thereof and oranges obtained by the cross-fertilization with Satsuma oranges. The term "β-cryptoxanthin-containing composition" herein indicates a composition having an artificially increased β-cryptoxanthin content. A method of processing Satsuma oranges to obtain the β-cryptoxanthin-containing composition by processing Satsuma oranges is not limited. For example, methods described in the above-described patent specifications 10 and 11 and methods described in non-patent literatures 2 to 4 can be employed.

When β-cryptoxanthin or the β-cryptoxanthin-containing composition is used as the medicine for preventing/treating the bone diseases, various components for the prescription can be used. They are pharmaceutically acceptable ordinary components such as a carrier, binder, stabilizer, excipient, diluent, pH buffer, disintegrator, solubilizer and isotonizing agent. In addition, the above-described, well-known substances having the effect of accelerating the osteogenesis and/or inhibiting the bone resorption, and minerals such as calcium, magnesium and phosphorus can also be used together with them. These preventive agents or remedies can be orally or parenterally administered. Namely, they can be orally administered in an ordinary administration form such as a powder, granules, capsules, a syrup or a suspension and also they can be parenterally administered in the form of, for example, a solution, an emulsion or a suspension by the injection, or they can be administered in the form of a spray to the nostrils. The oral administration is preferred. The dose can be suitably determined depending on the purpose of the administration (prevention or treatment), kind and seriousness of the bone disease and age of the patient.

The kinds of foods and food materials containing β-cryptoxanthin or a β-cryptoxanthin-containing composition and having the function of preventing or treating bone diseases, which are to be used for the prevention or treatment of bone diseases, are not particularly limited. The foods and food materials include drinks such as yogurt, yogurt drink, juices, cow's milk, soybean milk, liquors, coffee, black tea, green tea, oolong tea and sport drinks; baked cakes such as puddings, cookies, breads, cakes, jellies and rice crackers; Japanese cakes such as sweetened and jellied bean pastes; breads and cakes such as frozen sweets and chewing gums; noodles such as thick white noodles and buckwheat noodles; fish paste products such as boiled fish pastes, fish hanis and fish sausages; seasonings such as miso (fermented soybean paste), soy sauce, dressings, mayonnaise and sweetening agents; milk products such as cheeses and butters; and various side dishes such as bean curds, konnyaku (a gelatinous food made from devil's-tongue starch) as well as tsukudani (some foods boiled in sweetened soy sauce), gyoza (dumplings stuffed with minced pork), croquettes and salads. These foods and food materials may further contain the above-described well-known substances having the osteogenesis promoting effect and/or bone resorption inhibiting effect, as well as minerals such as calcium, magnesium and phosphorus.

The feed composition containing β-cryptoxanthin or that containing the β-cryptoxanthin-containing composition is advantageously usable for growing domestic animals and poultry such as pigs, cattle and chickens; pets such as dogs and cats; and farmed fish and shellfish. Such a feed composition may also contain the above-described well-known substances having the osteogenesis-accelerating effect and/or bone resorption-inhibiting effect such as ipriflavones as well as minerals such as calcium, magnesium, phosphorus, iron, zinc, manganese and copper.

The method of screening the active ingredient for the preventive/remedy for bone diseases such as osteoporosis in the present invention is not particularly limited so far as the method is a screening method wherein β-cryptoxanthin is used as the lead compound. By the screening method wherein β-cryptoxanthin is used as the lead compound, the development of a more effective osteogenesis promoter or a preventive/remedy for bone diseases is made possible. For efficiently screening the osteogenesis promoter or a preventive/remedy for bone diseases containing β-cryptoxanthin as the lead compound, for example, a combinatorial chemistry technique such as a method stated in the above described patent literature 12 can be used. Even when the combinatorial chemistry technique is not used, the screening of the osteogenesis promoter or the preventive/remedy for bone diseases with β-cryptoxanthin as the lead compound can be conducted by a classical technique structural activity correlation technique. The osteogenesis promoter or the preventive/remedy for bone diseases containing β-cryptoxanthin as the lead compound, which is obtained by the screening method, is also included in the present invention.

The following Examples will further specifically illustrate the present invention, which by no means limit the technical range of the present invention.

Example 1

Method (Culture of Osseous Tissue Pieces of Rats)

The femurs were extracted from rats (Wistar male rats; 4 to 5 weeks old) (purchased from Japan SLC Co., Ltd. and fed with solid Oriental yeast (MF)) under anesthesia with ether under a germfree condition. The femurs were each washed with 0.25 M sucrose solution, and then divided into the diaphysis (cortical bone) and metaphysis (cancellous bone). The bone tissue pieces were cultured in a culture medium (Dulbecco's modified culture medium containing 5% of glucose; serum-free medium) containing. β-cryptoxanthin, etc. at 3-7° C. in an incubator filled with 5% $CO_2$-95% air for 48 hours. β-cryptoxanthin used was "β-cryptoxanthin" of Extrasynthase Co., cycloheximide used was "Cycloheximide" of Sigma Co. Ltd., β-carotene was "β-carotene" of Sigma 社, xanthine was "Xanthine" of Sigma Co, Ltd., parathormone was "Parathormone" of Sigma Co. Ltd. and prostaglandin $E_2$ was "Prostaglandin $E_2$" of Sigma Co. Ltd. In the control, only the culture medium was used without β-cryptoxanthin or the like.

(Determination of Bone Calcium Level)

Bone calcium level in the bone tissue was determined. After the culture in the incubator, the tissue pieces were washed with 0.25 M sucrose solution and dried and then the bone was weighed. Then concentrated nitric acid was added to the tissue pieces. After the incineration at 120° C. for 12 hours, the bone calcium level was determined with an atomic absorption photometer ("Perkin-Elmer 303" of Perkin-Elmer Co.).

(Determination of Alkaline Phosphatase Activity)

The expression level of alkaline phosphatase, which is the most important enzyme for the acceleration of the calcification of bones, was examined. The tissue pieces cultured in the incubator were washed in 0.25 M sucrose solution, then pulverized in 3 ml of 65 mM barbital buffer (pH 7-4) and treated with ultrasonic waves. The resultant liquid was centrifuged. The supernatant, as the enzyme solution, was determined by a method of Walter ad Schutt in Method of Enzymatic Analysis, Vol. 1-2, p. 856, Academic Press, New York, 1965). Namely, this method was carried out as follows: p-nitrophenylphosphoric acid was used as the substrate. 0.05 ml of the enzyme solution was added to 2 ml of diethanolamine buffer (pH 9.8). After the incubation at 37° C. for 30 minutes, 10 ml of 0.05 N NaOH was added to the mixture. The absorbance (405 nm) was determined with a spectrophotometer to determine bone alkaline phosphatase activity of a bone remedy or a compound known to be effective for the bones.

(Determination of DNA Level)

DNA level was determined as an index of the number of cells in the bone tissue. After the culture in an incubator, the tissue pieces were washed with 0.25 M sucrose solution and then the wet weight of them was determined. They were pulverized in 4 ml of 0.1 N NaOH. After the osmosis at 4° C. for 24 hours, the liquid mixture was centrifuged. The supernatant was taken as the sample and determined by a method of Ceriotti et al. (J. Biol. Chem., 241; 34-77, 1951). Namely, 1 ml of concentrated hydrochloric acid and 1 ml of 0.04% indole solution were added to 2 ml of the sample and then the resultant mixture was heated to 100° C. in boiling water. After quenching followed by the extraction with 4 ml of chloroform, the chloroform layer was taken to determine bone DNA level with a spectrophotometer (490 nm).

(Oral Administration of β-Cryptoxanthin to Rats)

A solution of β-cryptoxanthin in corn oil having one of three kinds of concentration (10, 25 and 50 μg/ml corn oil) was orally administered to rats (Wistar male rats; 4 to 5 weeks old) in an amount/100 g body weight with a probe once a day for 7 days. The rats were sacrificed 24 hours after the final administration. The femurs were excised. The muscles, etc. were taken out and each femur was divided into diaphysis and metaphysis to determine the bone components.

Example 2

Results (Expression of the Osteogenesis Promoting Effect of β-Cryptoxanthin

The bone component-increasing effect of β-cryptoxanthin was examined. The diaphysis and metaphysis tissue of the femur was cultured in the above-described culture medium containing β-cryptoxanthin ($10^{-5}$ to $10^{-5}$ M) for 48 hours. Calcium level in the bone tissue, alkaline phosphatase activity (enzyme for accelerating the bone calcification) and the amount of deoxyribonucleic acid (DNA; index of number of cells in the bone tissue) were determined by the same methods as in Example 1. The results are shown in Table 1 and FIGS. 1 to 6. In each test group, the determination vas conducted 6 to 8 times and the results were represented by the average value and the standard error. The significant difference was determined by Student's t-test. The result was compared with that of the control. When P value was not higher than 0.01 (**) or not higher than 0.05 (*), the results were statistically significant. As a result, cryptoxanthin ($10^{-8}$ to $10^{-5}$ M) caused a significant increase in calcium level in the diaphysis and metaphysis tissue. Further, cryptoxanthin ($10^{-7}$ to $10^{-5}$ M) significantly increased the alkaline phosphatase activity in the diaphysis and also cryptoxanthin ($10^{-7}$ to $10^{-4}$ M) caused an increase in the enzymatic activity in the metaphysis. In addition, DNA level in the diaphysis tissue and the metaphysis tissue was significantly increased in the presence of cryptoxanthin ($10^{-7}$ to $10^{-5}$ M).

(Influence of Protein Synthesis Inhibitor)

The influence of a protein synthesis inhibitor on the expression of the effect of β-cryptoxanthin on the increase in the bone components was examined. As the protein synthesis inhibitor, cycloheximide that reacts on 60S liposome of eukaryotic cells and inhibits the transition reaction in the peptide chain elongation was used. Calcium level in the bone tissue, alkaline phosphatase activity and DNA level were determined in the presence of β-cryptoxanthin ($10^{-6}$ M) or cycloheximide ($10^{-6}$ M) or in the coexistence of β-cryptoxanthin ($10^{-6}$ M) and cycloheximide ($10^{-6}$ M). The results are shown in Table 2 and FIGS. 7 to 12. In each test group, the determination was conducted 6 times and the results were represented by the average value and the standard error. The significant difference was determined by Student's t-test. The result was compared with that of the control. When P value was not higher than 0.01 (*), the results were statistically significant, Calcium level, bone alkaline phosphatase activity and bone DNA level in the diaphysis and metaphysis tissue which had increased in the presence of β-cryptoxanthin ($10^{-6}$ M) were significantly lowered in the presence of cycloheximide ($10^6$ M). Those results proves that β-cryptoxanthin promotes the protein synthesis in the cancellous bone (metaphysis tissue) and cortical bone (diaphysis tissue) in the femur tissue to improve the osteogenesis.

TABLE 1

| | | β-cryptoxanthin | | | |
|---|---|---|---|---|---|
| | Control | $10^{-8}$ M | $10^{-7}$ M | $10^{-6}$ M | $10^{-5}$ M |
| Diaphysis tissue | | | | | |
| Bone calcium level (mg/g dry weight) | 228.2 ± 4.76 | 249.6 ± 3.33** | 269.9 ± 6.26** | 272.2 ± 3.15** | 291.7 ± 2.29** |
| Bone alkaline phosphatase activity (nmol/min/mg protein) | 554.8 ± 11.4 | 568.5 ± 9.5 | 604.2 ± 9.6* | 684.0 ± 17.7** | 644.6 ± 15.2** |
| Bone DNA level (mg/g bone wet weight) | 1.551 ± 0.056 | 1.741 ± 0.099 | 1.788 ± 0.049* | 1.746 ± 0.016* | 1.802 ± 0.063** |
| Metaphysis tissue | | | | | |
| Bone calcium level (mg/g dry weight) | 174.7 ± 4.47 | 204.7 ± 6.40** | 223.6 ± 9.27** | 216.8 ± 2.84** | 213.5 ± 5.59** |
| Bone alkaline phosphatase activity (nmol/min/mg protein) | 908.3 ± 5.1 | 918.4 ± 4.3 | 945.2 ± 5.4** | 1150.9 ± 26.8** | 1229.5 ± 40.9** |
| Bone DNA level (mg/g bone wet weight) | 3.061 ± 0.054 | 3.276 ± 0.207 | 4.170 ± 0.057** | 5.359 ± 0.207** | 5.584 ± 0.530** |

TABLE 2

| | Control | β-cryptoxanthin $10^{-6}$ M | Cycloheximide $10^{-6}$ M | Cycloheximide + Cryptoxanthin $10^{-6}$ M |
|---|---|---|---|---|
| Diaphysis tissue | | | | |
| Bone calcium level (mg/g dry weight) | 225.0 ± 5.01 | 275.1 ± 4.50* | 204.0 ± 15.59 | 192.8 ± 9.00** |
| Bone alkaline phosphatase activity (nmol/min/mg protein) | 560.1 ± 8.9 | 691.5 ± 11.2* | 534.5 ± 64.2 | 530.0 ± 10.0 |

TABLE 2-continued

|  | Control | β-crypto-xanthin $10^{-6}$ M | Cyclo-heximide $10^{-6}$ M | Cycloheximide + Cryptoxanthin $10^{-6}$ M |
|---|---|---|---|---|
| Bone DNA level (mg/g bone wet weight) | 1.403 ± 0.065 | 1.800 ± 0.025* | 1.299 ± 0.127 | 1.402 ± 0.133 |
| Metaphysis tissue | | | | |
| Bone calcium level (mg/g dry weight) | 178.0 ± 5.11 | 220.0 ± 3.25* | 156.4 ± 2.81 | 168.0 ± 10.67 |
| Bone alkaline phosphatase activity (nmol/min/mg protein) | 898.1 ± 11.3 | 1168.2 ± 30.1* | 948.8 ± 21.1 | 957.0 ± 37.0 |
| Bone DNA level (mg/g bone wet weight) | 3.020 ± 0.049 | 5.401 ± 0.188* | 3.001 ± 0.454 | 3.499 ± 0.259 |

Comparative Example

Figure 13:
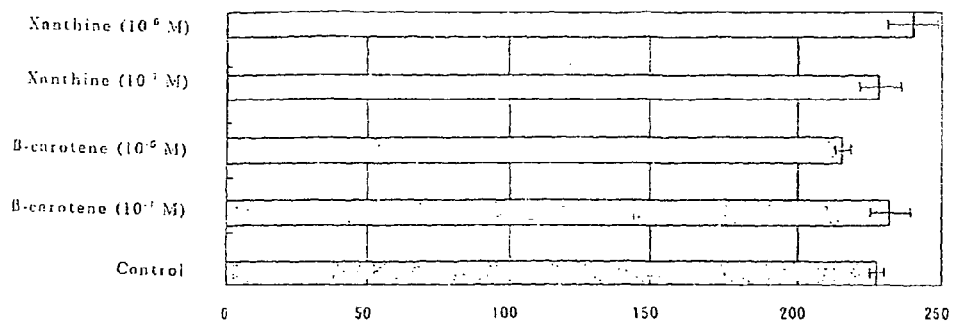
FIG. 13 shows the results of the determination of bone calcium level in the diaphysis tissue in the coexistence of β-cryptoxanthin of the present invention and β-carotene or in the coexistence of β-cryptoxanthin and xanthine.
Figure 14:
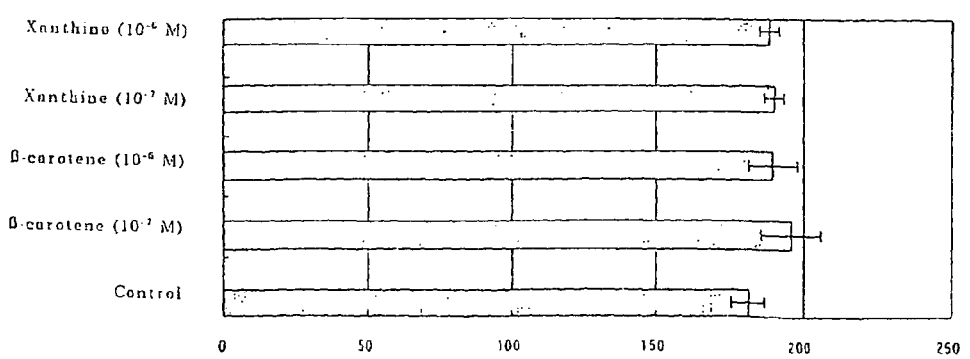
FIG. 14 shows the results of the determination of bone calcium level in the metaphysis tissue in the coexistence of β-cryptoxanthin of the present invention and β-carotene or in the coexistence of β-cryptoxanthin and xanthine.
Figure 15:
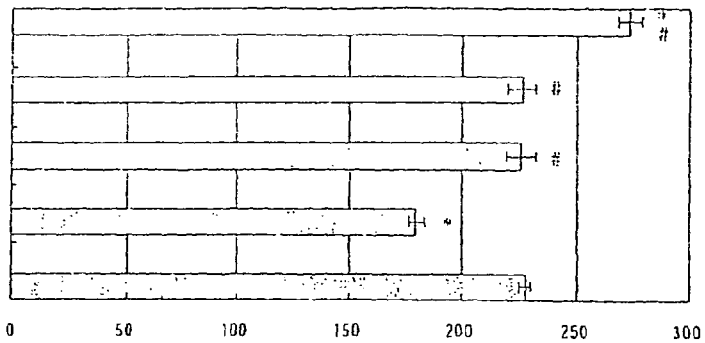
FIG. 15 shows the results of the determination of bone calcium level in the diaphysis tissue in the coexistence of β-cryptoxanthin of the present invention and parathyroid hormone.
Figure 16:
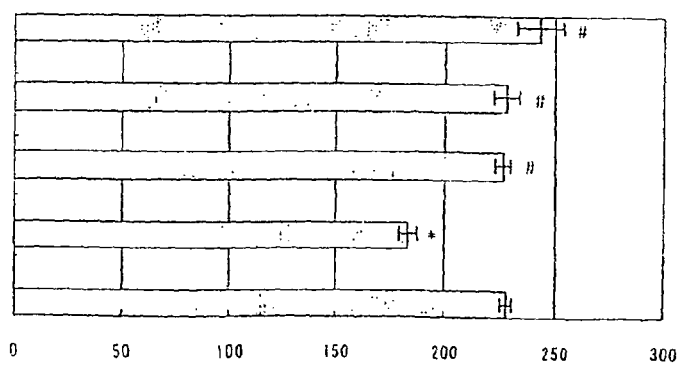
FIG. 16 shows the results of the determination of bone calcium level in the metaphysis in the coexistence of β-cryptoxanthin of the present invention and parathyroid hormone.
Figure 17:
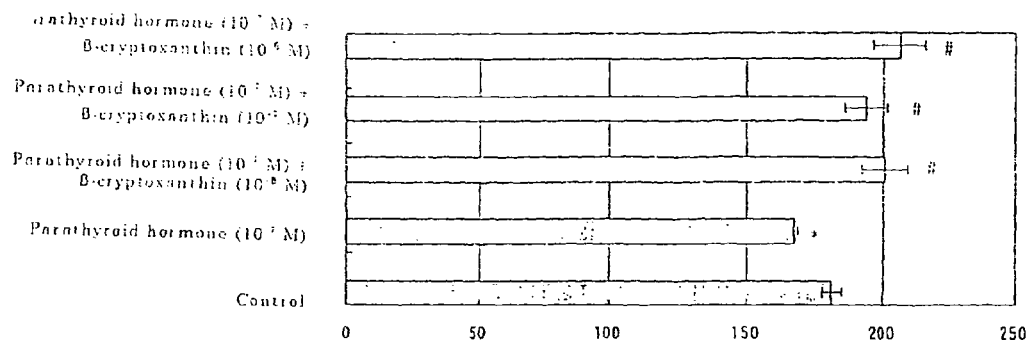
FIG. 17 shows the results of the determination of bone calcium level in the diaphysis tissue in the coexistence of β-cryptoxanthin of the present invention and prostaglandin $E_2$.
Figure 18:
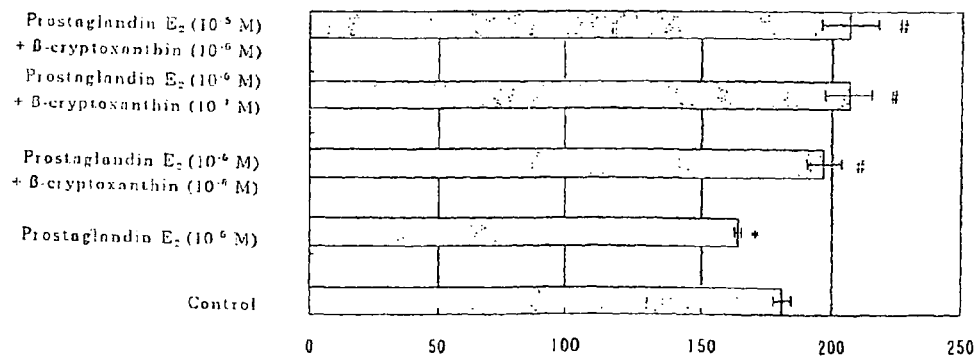
FIG. 18 shows the results of the determination of bone calcium level in the metaphysis tissue in the coexistence of β-cryptoxanthin of the present invention and prostaglandin $E_2$.
Figure 19:
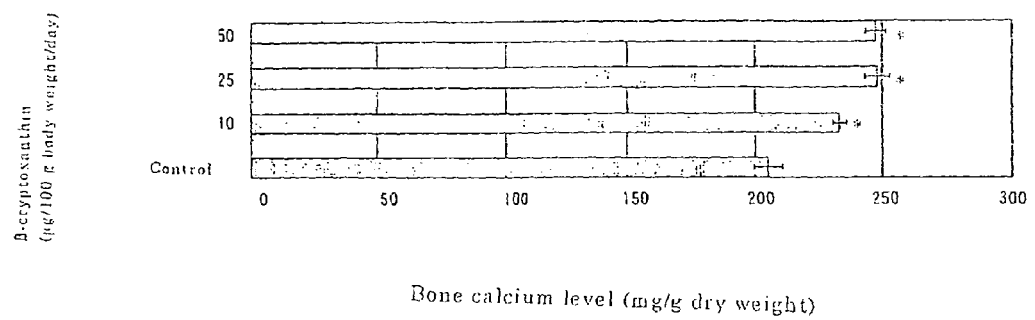
FIG. 19 shows the results of the determination of bone calcium level in the diaphysis tissue after the oral administration of β-cryptoxanthin of the present invention to rats.
Figure 20:
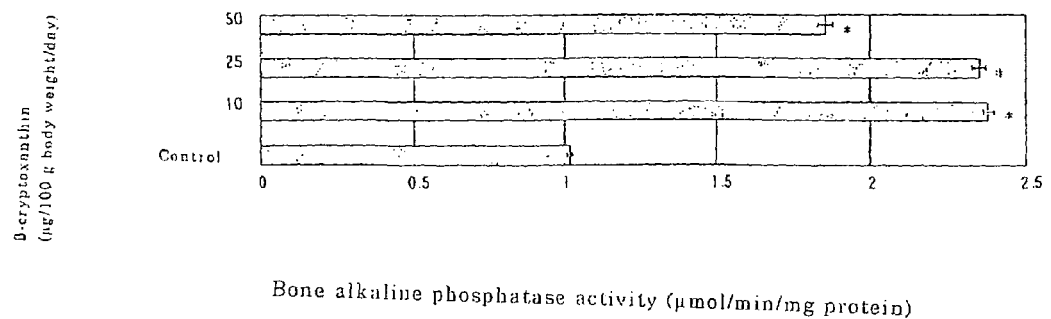
FIG. 20 shows the results of the determination of bone alkaline phosphatase activity in the diaphysis tissue after the oral administration of β-cryptoxanthin of the present invention to rats.
Figure 21:
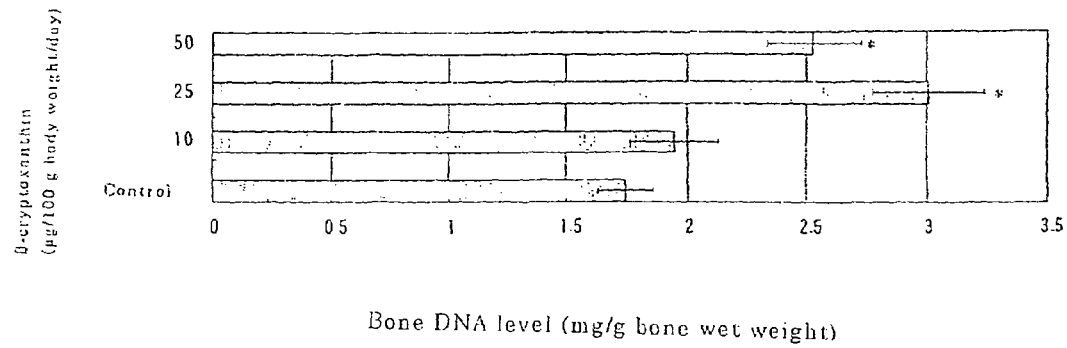
FIG. 21 shows the results of the determination of bone DNA level in the diaphysis tissue after the oral administration of β-cryptoxanthin of the present invention to rats.
Figure 22:
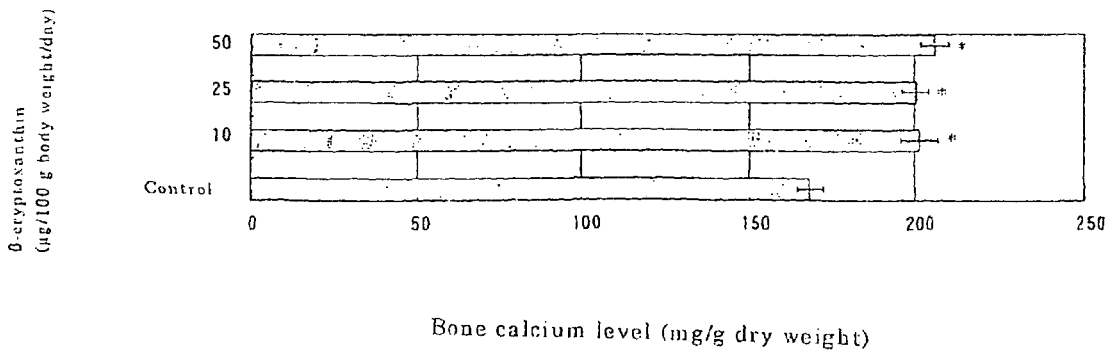
FIG. 22 shows the results of the determination of bone calcium level in the metaphysis tissue after the oral administration of β-cryptoxanthin of the present invention to rats.
Figure 23:
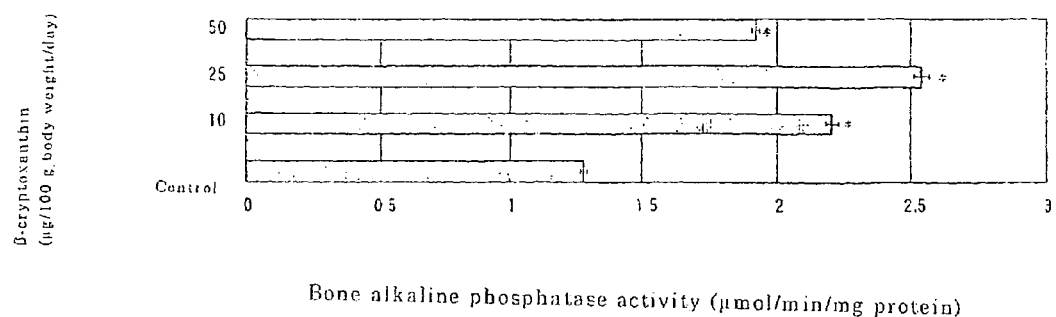
FIG. 23 shows the results of the determination of bone alkaline phosphatase activity in the metaphysis tissue after the oral administration of β-cryptoxanthin of the present invention to rats.
Figure 24:
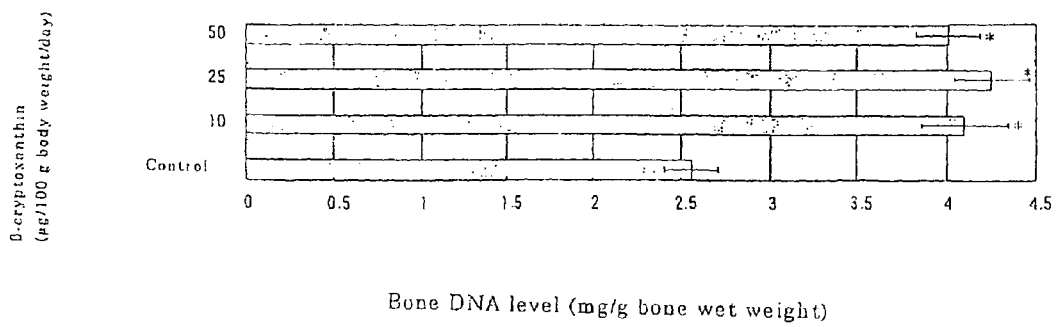
FIG. 24 shows the results of the determination of bone DNA level in the metaphysis tissue after the oral administration of β-cryptoxanthin of the present invention to rats.

The effect of each of β-carotene and xanthine (2,6-dihydroxypurine), instead of β-cryptoxanthin, on the bone calcium level was examined. The diaphysis or metaphysis tissue was cultured in a culture medium containing $10^{-7}$ M of β-carotene or $10^{-6}$ M of xanthine in the same method as that in Example 1 for 48 hours and then the calcium level in the bone tissue was determined. The results are shown in Table 3 and FIGS. 13 and 14. The numerals in Table 3 show the average ±standard error of 6 to 8 rats. It is apparent from Table 3 that the significant effect of β-carotene or xanthine on increasing calcium level in the bone tissue could not be obtained.

ture was conducted in the same manner as that described above in the coexistence of them and β-cryptoxanthin ($10^{-8}$ M to $10^{-6}$ M) and then calcium level in the bone tissue was determined. The results are shown in Table 4 and FIGS. 15 to 18. In each test group, the determination was conducted 6 to 8 times and the results were represented by the average value and the standard error. The significant difference was determined by Student's t-test. The result was compared with that of the control. When P value was not higher than 0.01 (*) as compared with the control or it is not higher than 0.1 (#) as compared with that of prostaglandin $E_2$, the results were statistically significant. When the bone tissue was cultured in the presence of PTH, the calcium level in the diaphysis and metaphysis tissue significantly reduced. This reduction was

TABLE 3

|  | Control | β-carotene | | Xanthine | |
|---|---|---|---|---|---|
|  |  | $10^{-7}$ M | $10^{-6}$ M | $10^{-7}$ M | $10^{-6}$ M |
| Diaphysis tissue | | | | | |
| Bone calcium level (mg/g dry weight) | 227.9 ± 2.60 | 232.2 ± 6.66 | 215.6 ± 2.78 | 228.6 ± 7.08 | 240.2 ± 8.46 |
| Metaphysis tissue | | | | | |
| Bone calcium level (mg/g dry weight) | 181.1 ± 5.57 | 195.4 ± 10.10 | 189.4 ± 8.06 | 189.8 ± 3.30 | 188.2 ± 3.34 |

(Expression of Bone Resorption-Inhibiting Effect of β-Cryptoxanthin)

The bone mineral dissolution-inhibiting effect of β-cryptoxanthin was examined. Parathyroid hormone (PTH) is a peptide hormone secreted from the accessory thyroid to exhibit the effect of the bone mineral dissolution (bone resorption). PTH also has a pathophysiologic role on the expression of osteoporosis caused by the aging. It is known that prostaglandin $E_2$ also causes physiologic bone mineral dissolution. The diaphysis or metaphysis tissue of the femur was cultured in the presence of $10^{-7}$ M PTH or $10^{-5}$ M prostaglandin $E_2$ for 48 hours and then calcium level in the bone tissue was determined. In another experiment, the culsignificantly controlled in the presence of β-cryptoxanthin ($10^{-8}$ to $10^{-6}$ M). A significant reduction in calcium level in the bone tissue was also caused by prostaglandin $E_2$ ($10^{-5}$ M) which causes the physical bone mineral dissolution. This reduction could be completely controlled in the presence of β-cryptoxanthin ($10^{-5}$ to $10^{-6}$ M).

From the above-described results, it was confirmed that β-cryptoxanthin increases and accelerates the bone formation and also inhibits the bone resorption to exhibit the effect of retaining and increasing the amount of bone mineral and thus it functions as an anti-osteoporotic factor.

TABLE 4

| | | Diaphysis tissue | | | |
|---|---|---|---|---|---|
| | | Parathyroid hormone | Parathyroid hormone + β-cryptoxanthin | | |
| | Control | $10^{-7}$ M | $10^{-8}$ M | $10^{-7}$ M | $10^{-6}$ M |
| Bone calcium level (mg/g dry weight) | 228.0 ± 2.56 | 180.0 ± 3.23* | 226.1 ± 6.43# | 226.3 ± 5.89# | 274.2 ± 5.02*# |
| | | Diaphysis tissue | | | |
| | | Prostaglandin $E_2$ | Prostaglandin $E_2$ + β-cryptoxanthin | | |
| | Control | $10^{-5}$ M | $10^{-8}$ M | $10^{-7}$ M | $10^{-6}$ M |
| Bone calcium level (mg/g dry weight) | 228.0 ± 2.56 | 182.8 ± 4.06* | 226.3 ± 3.33# | 227.8 ± 5.52# | 243.1 ± 11.04# |
| | | Metaphysis tissue | | | |
| | | Parathyroid hormone | Parathyroid hormone + β-cryptoxanthin | | |
| | Control | $10^{-7}$ M | $10^{-8}$ M | $10^{-7}$ M | $10^{-6}$ M |
| Bone calcium level (mg/g dry weight) | 180.6 ± 3.61 | 167.0 ± 0.96* | 200.6 ± 8.66# | 193.6 ± 8.02# | 206.0 ± 9.81# |
| | | Metaphysis tissue | | | |
| | | Prostaglandin $E_2$ | Prostaglandin $E_2$ + β-cryptoxanthin | | |
| | Control | $10^{-6}$ M | $10^{-8}$ M | $10^{-7}$ M | $10^{-6}$ M |
| Bone calcium level (mg/g dry weight) | 180.6 ± 3.61 | 163.5 ± 1.47* | 196.6 ± 6.87# | 206.4 ± 9.13# | 206.8 ± 11.10# |

(Increase in Bone Components by the Oral Administration of β-Cryptoxanthin to Rats)

Tests were conducted to examine whether the bone components are increased by the oral administration of β-cryptoxanthin to rats or not. β-cryptoxanthin was administered for 7 days (10, 25 or 50 µg/100 g body weight/day) and then calcium level in the bone tissue, determination of alkaline phosphatase activity (enzyme for the acceleration of the calcification of bones) and the amount of deoxyribonucleic acid (DNA: index of the number of the cells in the bone tissue) were determined by the same methods as those in Example 1. The results are shown in Table 5 and FIGS. 19 to 24. In each test group, the determination was conducted 6 times and the results were represented by the average value and the standard error. The significant difference was determined by Student's t-test. The result was compared with that of the control. When P value was not higher than 0.01 (*) as compared with the control, the results were statistically significant. As a result, calcium level in the diaphysis and metaphysis tissue was significantly increased by the administration of β-cryptoxanthin (10, 25 or 50 µg/100 g body weight/day). The alkali phosphatase activity (enzyme for the acceleration of the calcification of bones) in the diaphysis and metaphysis tissue was significantly increased by the administration of β-cryptoxanthin (10, 25 or 50 µg/100 g body weight/day). DNA in the bone tissue (index of the number of the cells in the bone tissue) was significantly increased by the administration of β-cryptoxanthin (25 or 50 µg/100 g body weight/day) in the diaphysis, and it also significantly increased by the administration of β-cryptoxanthin (10, 25 or 50 µg/100 g body weight/day) in the metaphysis.

From the above-described results, it was confirmed that by the oral administration of β-cryptoxanthin, the amount of the bone components was increased to exhibit the effect of increasing the amount of bones. From this fact, β-cryptoxanthin is considered to be useful as an osteogenesis promoter and effective in preventing and treating osteoporosis.

TABLE 5

| | | β-cryptoxanthin (µg/100 g body weight/day) | | |
|---|---|---|---|---|
| | Control | 10 | 25 | 50 |
| | Diaphysis tissue | | | |
| Bone calcium level (mg/g dry weight) | 205.1 ± 5.40 | 232.8 ± 3.00* | 248.3 ± 5.10* | 247.5 ± 4.20* |
| Bone alkaline phosphatase activity (µmol/min/mg protein) | 1.02 ± 0.010 | 2.38 ± 0.019* | 2.35 ± 0.021* | 1.85 ± 0.025* |
| Bone DNA level (mg/g bone wet weight) | 1.75 ± 0.11 | 1.95 ± 0.18 | 3.01 ± 0.23* | 2.53 ± 0.20* |

TABLE 5-continued

| | β-cryptoxanthin (μg/100 g body weight/day) | | | |
|---|---|---|---|---|
| | Control | 10 | 25 | 50 |
| Metaphysis tissue | | | | |
| Bone calcium level (mg/g dry weight) | 168.3 ± 4.00 | 201.5 ± 5.60* | 200.3 ± 3.90* | 205.9 ± 4.10* |
| Bone alkaline phosphatase activity (μmol/min/mg protein) | 1.28 ± 0.013 | 2.21 ± 0.023* | 2.545 ± 0.029* | 1.92 ± 0.015* |
| Bone DNA level (mg/g bone wet weight) | 2.56 ± 0.15 | 4.10 ± 0.24* | 4.25 ± 0.21* | 4.01 ± 0.18* |

INDUSTRIAL APPLICABILITY

The present invention can provide an osteogenesis promoter containing β-cryptoxanthin as the active ingredient and having a remarkable effect of accelerating the osteogenesis to prevent and treat bone diseases and also agents having both osteogenesis promoting effect and bone resorption inhibiting effect and usable for preventing and treating bone diseases such as osteoporosis.

What is claimed is:

1. A method of ameliorating bone loss problems associated with aging in a person in need thereof, comprising administering to the person in need thereof an amount of purified β-cryptoxanthin effective to ameliorate the bone loss problems associated with aging.

2. A method as defined in claim 1, wherein the amount is between about 100 and about 1000 μg per kilogram of body weight.

3. A method as defined in claim 1, wherein the amount is between about 0.5 mg and about 10 mg.

4. A method of ameliorating osteoporosis in a person in need thereof, comprising administering to the person in need thereof an amount of purified β-cryptoxanthin effective to ameliorate the osteoporosis.

5. A method as defined in claim 4, wherein the amount is between about 100 and about 1000 μg per kilogram of body weight.

6. A method as defined in claim 4, wherein the amount is between about 0.5 mg and about 10 mg.

7. A method of promoting osteogenesis in a person in need thereof, comprising administering to the person in need thereof an amount of purified β-cryptoxanthin effective to promote osteogenesis.

8. A method as defined in claim 7, wherein the amount is between about 100 and about 1000 μg per kilogram of body weight.

9. A method as defined in claim 7, wherein the amount is between about 0.5 mg and about 10 mg.

* * * * *